United States Patent
Arstad

(10) Patent No.: US 8,309,054 B2
(45) Date of Patent: *Nov. 13, 2012

(54) METHOD FOR THE PURIFICATION OF RADIOLABELLED COMPOUNDS

(75) Inventor: Erik Arstad, London (GB)

(73) Assignee: Hammersmith Imanet Limited, London (GB)

( * ) Notice: Subject to any disclaimer, the term of this patent is extended or adjusted under 35 U.S.C. 154(b) by 436 days.

This patent is subject to a terminal disclaimer.

(21) Appl. No.: 12/375,555

(22) PCT Filed: Jul. 25, 2007

(86) PCT No.: PCT/GB2007/002845
§ 371 (c)(1),
(2), (4) Date: Jan. 29, 2009

(87) PCT Pub. No.: WO2008/015391
PCT Pub. Date: Feb. 7, 2008

(65) Prior Publication Data
US 2009/0312564 A1    Dec. 17, 2009

Related U.S. Application Data

(60) Provisional application No. 60/821,280, filed on Aug. 3, 2006.

(51) Int. Cl.
*A61K 51/00* (2006.01)
*A61M 36/14* (2006.01)

(52) U.S. Cl. ............ 424/1.11; 424/1.65; 424/1.81; 424/1.85; 424/1.89

(58) Field of Classification Search ............ 424/1.11
See application file for complete search history.

(56) References Cited

U.S. PATENT DOCUMENTS

| 6,749,830 B2 | 6/2004 | Wilson et al. |
| 2005/0226776 A1 * | 10/2005 | Brady et al. .............. 422/99 |

FOREIGN PATENT DOCUMENTS

| EP | 0949632 | 5/2003 |
| WO | 02/16333 | 2/2002 |
| WO | 2004/029006 | 4/2004 |
| WO | WO 2005061110 A1 * | 7/2005 |

OTHER PUBLICATIONS

Sandell et al. J. Labelled Cpd. Radiopharm. 43, 2000, 331-338.*
Bergman et al. Appl. Radiat. Isot. 2001, 927-933.*
Wilson et al. Nucl. Med. Biol. 2000, 529-532.*
Sandell et al. J. Labell. Cpd. Radiopharm. 2000, 331-338.*
Rozing, G. "Trends in HPLC Column formats-Microbore, Nanobore and Smaller" Recent Developments in LC Column Technology, 2003, pp. 2-7.
GB0615352.2 Search Report dated Nov. 2006.
PCT/GB2007/002845 Int'l Search Report/Written Opinion dated Dec. 2007.

* cited by examiner

*Primary Examiner* — Michael G Hartley
*Assistant Examiner* — Sean R Donohue

(57) ABSTRACT

The invention relates to methods and apparatus for purifying a radiolabelled compound. The method comprises (i) passing a crude reaction mixture comprising the desired radiolabelled compound and one or more contaminants in a solvent through a narrow bore vessel at elevated temperature such that the organic solvent and either the radiolabelled compound or one or more contaminants is vaporised forming a vaporised component, and (ii) collecting the resulting vaporised component by condensing into a collection vessel.

4 Claims, 1 Drawing Sheet

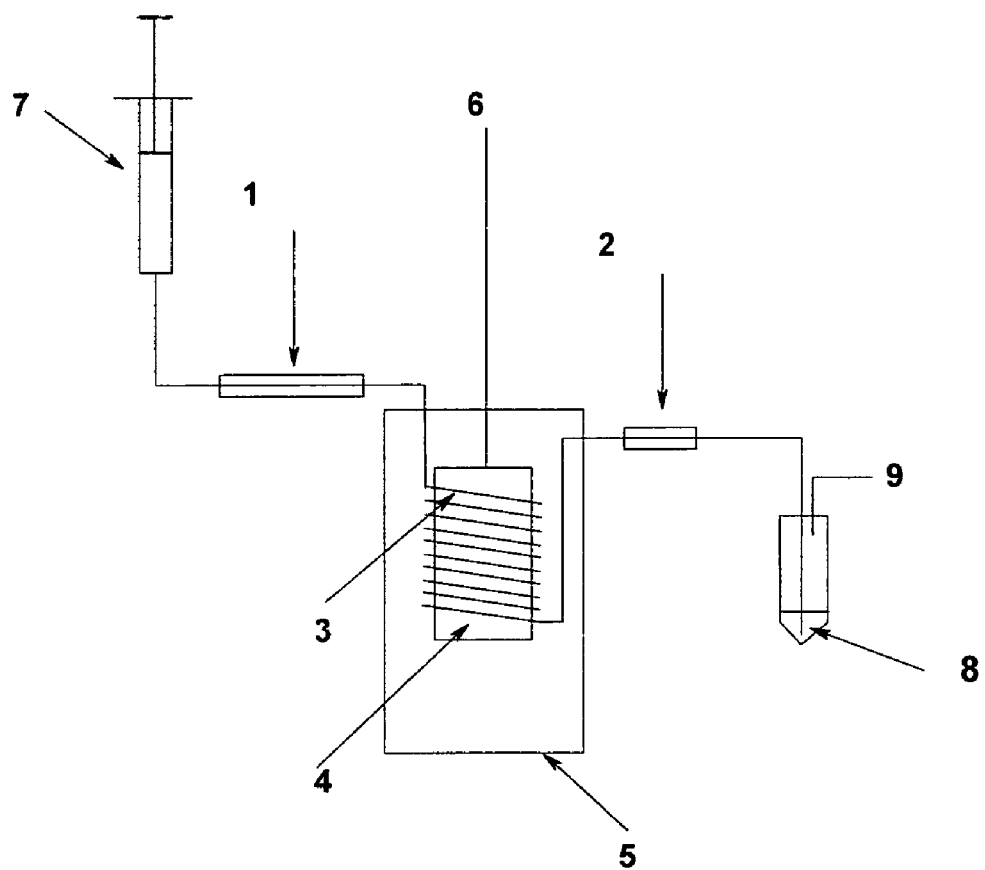
Scheme of the distillation apparatus

METHOD FOR THE PURIFICATION OF RADIOLABELLED COMPOUNDS

This application is a filing under 35 U.S.C. 371 of international application number PCT/GB2007/002845, filed Jul. 25, 2007, which claims priority to application No. 60/821,280 filed Aug. 3, 2006, in The United States, the entire disclosure of which is hereby incorporated by reference.

The present invention relates to methods for purifying radiolabelled compounds, particularly those radiolabelled with [$^{18}$F]-fluoride and [$^{11}$C]-carbon and to apparatus for performing such methods.

Radiolabelled compounds are routinely purified using one of three main techniques;

1) Chromatography by means of High Performance Liquid Chromatography (HPLC). HPLC is based on the principle that different compounds have different solubility/affinity for stationary phases as well as solvent mixtures and hence by eluting the crude reaction mixture through a column containing a suitable stationary phase the compounds elute at different times and hence can readily be separated. Whilst HPLC is a very powerful technique for separation it represents several problems for the preparation of radiolabelled compounds. Firstly, HPLC purification is time consuming and typically takes between 15 and 30 minutes, which in the case of radiolabelled compounds results in a significant loss of radioactivity due to decay. Secondly, the purified radiolabelled compound is diluted to volumes that are too large for subsequent reactions, and for reaction intermediates an additional concentration step is required. Thirdly, HPLC is difficult to automate and any procedure involving HPLC therefore requires manual handling/supervision or highly complicated equipment. Finally, HPLC equipment takes up relatively large space compared with other equipment used for radiolabelling, which restrains the number of productions rigs and other equipment that can be placed in a hot-cell.

2) Chromatography by means of cartridges/Sep-Pak. This technique is based on the same principles as HPLC, but rather than using a highly pressurised column this technique utilises a small cartridge containing a suitable stationary phase with elution of a solvent using mild pressure. Whilst this method is less time consuming and space demanding than HPLC it represents several of the same problems to radiosynthesis as HPLC. Firstly, the isolated radiolabelled compound is usually obtained in diluted form and hence further concentration is required for reaction intermediates. Secondly, the method involves a number of technical steps, i.e. diluting the product mixture in a suitable solvent (usually aqueous phase), passing the diluted mixture through the cartridge, washing the cartridge with a suitable solvent (usually water) and thirdly eluting the radiolabelled compound in a suitable solvent (usually an organic solvent). While this is easier to automate than HPLC, the additional steps introduce significant extra complication to any automated equipment. Fourthly, as the cartridge usually has to be washed with an aqueous solution as part of the procedure, a drying step is often required. Finally, the overall procedure is relatively time consuming and hence results in significant loss of radioactivity due to radioactive decay.

3) Purification by means of distillation. Conventional distillation of radiolabelled compounds is often problematic. Distillation is usually carried out by heating a reaction vessel containing the product under reduced pressure or under a stream of an inert gas such as nitrogen, argon or helium. Successful distillation requires heating slightly above the boiling point of the solvent, lower temperature gives low distillation rate and a higher temperature often results in vigorous boiling with the effect that parts of the crude mixture is carried over with the product. It is also difficult to effectively collect the radiolabelled compound as the inert gas stream must by sufficient to carry the radiolabelled compound over to a collecting vessel but if the gas stream is too strong condensation efficiency is reduced as the gas carries the radiolabelled compound beyond the collection vessel. As a result distillation yields are difficult to make reproducible, the procedure is time consuming and automation is complicated. As the equipment required for distillation typically has a relatively large volume compared with the volume of the reaction mixture, losses in the process are significant. Finally, as the procedure entails prolonged heating of reaction mixtures decomposition is often o problem, particularly with labile radiolabelled compounds such as acid halides.

Radiochemical processes which make use of narrow bore reaction vessels are known. For example, US 2002/0155063 describes a process in which $^{11}$C methyl iodide and a PET precursor compound are reacted together in an HPLC injection loop. However, the resulting $^{11}$C methylated product is then purified by conventional HPLC.

Thus, there exists a need for new methods for purifying radiolabelled compounds, particularly for methods which are susceptible to automation and can be incorporated into or used in conjunction with automated radiosynthesis apparatus.

BRIEF DESCRIPTION OF THE DRAWINGS

FIG. 1 depicts a schematic of an apparatus suitable for performing a method according to the invention having restrictors 1 and 2, HPLC injector loop 3, electrical heating cylinder 4, heating module 5, a temperature control unit 6, glass syringe 7, product vial 8, and vent 9.

According to the invention, there is provided a method for purifying a radiolabelled compound which comprises (i) passing a crude reaction mixture comprising the desired radiolabelled compound and one or more contaminants in a solvent through a narrow bore vessel at elevated temperature such that the solvent and either the radiolabelled compound or one or more contaminants is vaporised forming a vaporised component, and (ii) collecting the resulting vaporised component by condensing into a collection vessel.

In contrast to the purification methods for radiolabelled compounds described in the prior art, the methods of the present invention are simple, easy to automate, do not lead to dilution of the product and involve short exposure to heat. No carrier gas is required as the evaporated solvent itself serves to carry the vaporised component through the narrow bore vessel. Following vaporisation, the vaporised component can be directed into a collection vessel, which can be sealed or open as required, and by keeping the collection vessel below the boiling point of the solvent, condensation by nature will prevent built up of pressure. The vaporised component can be led into a collection vessel of choice using valves, which greatly simplifies automation. As there is no carrier gas or reduced pressure in the system effective collection of the vaporised component is ensured. The method is highly robust as the sensitivity to temperature changes is limited and there is no need to tightly control gas flow. As the exposure of the reaction mixture to heat occurs over a very short time-period decomposition of labile compounds should be minimal. An additional benefit is the speed with which purification can be achieved, which only is limited to the rate of vaporisation. Finally, as the total volume of the apparatus is small, loss of radioactivity in the process is kept to a minimum.

The narrow bore vessel preferably takes the form of a tube with a narrow bore, for example an HPLC loop with no solid support packing. The internal diameter of the narrow bore vessel is usually in the range of about 1 micrometer to 1.5 mm, preferably 40 to 200 µm. It is particularly convenient if the narrow bore vessel is open at both ends so that the crude mixture can be flushed through.

The length of the narrow bore vessel will be chosen such that it is long enough for the purification to be effected but is sufficiently short to minimise residence time in the vessel. A convenient length for the narrow bore vessel is from about 5 cm to 50 cm long, more usually 5 cm to 20 cm and typically about 15 cm.

Suitable solvents for use in the methods of the invention include acetonitrile, ethanol, tetrahydrofuran, diethylether, dichloromethane, chloroform, water, acetone, ethyl acetate, and dimethylformamide. In a separate aspect of the invention supercritical carbon dioxide may be used as solvent.

In one embodiment of the invention, restrictor tubes at inlet and outlet of the narrow bore vessel may be used to promote the build-up of pressure necessary for generating the vaporised component. These tubes have a smaller inner diameter (typically 0.1-0.2 mm) than the narrow bore vessel. By choosing a longer restrictor tube for the sample inlet compared with the outlet, the flow of the distilling vaporised component will be guided during feeding-in of the crude mixture.

The elevated temperature used in the method is suitably in the range of 80° C. to 400° C., preferably 50° C. to 250° C., more preferably 90° C. to 150° C. In one aspect of the invention, the elevated temperature used is such that the solvent reaches a supercritical state. Where supercritical carbon dioxide is used as solvent, the temperature used in the method can be as low as −80° C.

The methods of the invention may be utilised for rapid and efficient purification of radiolabelled compounds during radiosynthesis. Following labelling of a precursor compound with a radionuclide the crude reaction mixture is passed through a heated narrow bore vessel thereby producing a vaporised component of all volatile compounds whereas non-volatile compounds remain in the narrow bore vessel. The crude reaction mixture may be introduced into the narrow bore vessel by any convenient means, for example by injection, applying external pressure to the narrow bore vessel using pressurised gas or heating the narrow bore vessel to generate vapour. The flow rate of the crude reaction mixture is preferably in the range 0.1 to 1.0 ml/min.

If the crude reaction mixture contains a volatile radiolabelled compound it will form part of the vaporised component and can therefore readily be directed into a collection vessel where the radiolabelled compound and the solvent is condensed. By designing the radiolabelling reaction such that the precursor compound is non-volatile, e.g. by using non-volatile fragments such as a para-toluenesulphonic acid leaving group or a charged fragment such as a quaternary amine as part of the precursor compound, the precursor compound will remain in the heated narrow bore vessel. In effect, this provides an efficient and rapid way of isolating the radiolabelled compound from a crude reaction mixture.

Thus, in one aspect of the invention, the radiolabelled compound is suitably a low molecular weight compound with a boiling point of up to 200° C. such that the radiolabelled compound, along with an organic solvent, is separated from higher boiling contaminants during the method. The purified radiolabelled compound may be collected in a suitable vessel such as a vial ready for further use. The narrow bore vessel may be cleaned by passing a suitable solvent down its length, alternatively disposable narrow bore vessels may be used. Suitable low molecular weight radiolabelled compounds include many radiolabelling $[^{18}F]$-synthons such as $[^{18}F]$-fluoroalkyls, $[^{18}F]$-fluoroalkenyls, $[^{18}F]$-fluoroalkylazides, $[^{18}F]$-fluoroarylaldehydes, $[^{18}F]$-fluoroalkylaldehydes, $[^{18}F]$-fluoroalkylthiols, or $[^{11}C]$-synthons such as $[^{11}C]$-alkylhalides.

Alternatively, the radiolabelling reaction can be designed such that the radiolabelled compound is non-volatile whereas the precursor compound is volatile, e.g. by forming a quarternary amine or other non-volatile group in the radiolabelled compound from a volatile precursor compound such as a tertiary amine. The synthesis of C-11 cholin and F-18 fluoroalkyl cholin are good examples of such reactions. In this way the radiolabelled compound can be obtained solvent free in the heated tubing, whereas the solvent and excess precursor compound is directed into a separate vessel and/or waste in the form of the vaporised component.

Thus, in an alternative aspect of the invention, the radiolabelled compound is suitably a high molecular weight compound, with a boiling point of 200° C. or more. In this aspect, the radiolabelled compound is left behind in the narrow bore vessel while lower boiling impurities may be collected in a suitable vessel such as a vial ready for disposal. In this aspect of the invention, the purified radiolabelled compound may subsequently be removed from the narrow bore vessel by eluting it with a suitable solvent or used to perform a radiochemical reaction inside the narrow bore vessel. Suitable radiolabelled compounds for this aspect of the invention include radiolabelled tracers such as 2-$[^{18}F]$-fluoro-2-deoxy-D-glucose ($[^{18}F]$-FDG), 3'-deoxy-3-$[^{18}F]$fluorothymidine ($[^{18}F]$-FLT), 2-$[^{18}F]$-fluoroethyl-L-tyrosine ($[^{18}F]$-FET), $[^{18}F]$-fluorooestradiol ($[^{18}F]$-FES), 9-[4-$[^{18}F]$fluoro-3-(hydroxymethyl)butyl]guanine ($[^{18}F]$-FHBG), $[^{11}C]$-PIB or its analogues as described in WO 02/16333, 2β-carbomethoxy-3β-(4-fluorophenyl)tropane ($[^{11}C]$-CFT), $[^{11}C]$-raclopride, or $[^{11}C]$-thymidine.

In a further aspect of the invention, there is provided a method as described above, which comprises the further step of (iii) reaction of the resulting purified radiolabelled compound in a narrow bore vessel to form a second radiolabelled compound. The narrow bore vessel used in step (iii) may be the same narrow bore vessel as used in steps (i) and (ii), or a separate narrow bore vessel in fluid connection therewith. For example in this aspect of the invention, steps (i) and (ii) may be used to purify a radiolabelling synthon such as a $[^{18}F]$-synthon or $[^{11}C]$-synthon, suitably a $[^{18}F]$-fluoroalkyl, $[^{18}F]$-fluoroalkenyl, $[^{18}F]$-fluoroalkylazide, $[^{11}C]$-alkylhalide, $[^{18}F]$-fluoroarylaldehyde, $[^{18}F]$-fluoroalkylaldehyde, or $[^{18}F]$-fluoroalkylthiol, which is then used in step (iii) to react with a further precursor compound to prepare a radiolabelled tracer such as a $[^{18}F]$-tracer or $[^{11}C]$ tracer.

According to a further aspect of the invention, there is provided an apparatus for purifying a radiolabelled compound which comprises a narrow bore vessel containing a crude reaction mixture which crude reaction mixture comprises the desired radiolabelled compound and one or more contaminants in a solvent. Suitably, the narrow bore vessel is a tube with a narrow bore, such as an HPLC loop with no solid support packing. More suitably, the internal diameter of the narrow bore vessel is in the range of about 1 micrometer to 1.5 mm, preferably 40 to 200 µm.

The following example is described with reference to FIG. 1 which is a schematic of an apparatus suitable for performing a method according to the invention.

EXAMPLE

Preparation of $[^{18}F]$2-Fluoroethylazide
Distillation Apparatus
A scheme of the apparatus is shown in FIG. 1. The tubing material consists of standard HPLC parts. Restrictors 1 and 2 are narrow bore stainless steel tubes (i.d. 0.127 mm) of 13.5 cm and 7.0 cm length, respectively. The HPLC injector loop 3 has a capacity of 1.0 mL. The electrical heating cylinder 4 can be heated up to 200° C. by a heating module 5 with a temperature control unit 6.

Preparation of [$^{18}$F]2-Fluoroethylazide

Toluene-4-sulfonic acid 2-azido-ethyl ester (1.5 μl, 7.5 μmol) in acetonitrile (0.2 ml) is stirred with [$^{18}$F]KF-Kryptofix complex (5 mg) and potassium carbonate (1 mg) for 15 minutes at 80° C. The reaction mixture is loaded into a glass syringe 7 (Hamilton, Gastight, 1 ml) and passed through the apparatus at 130° C. with a flow rate of 0.2 ml/min. Acetonitrile (0.05 ml) is used as trapping solvent in the product vial 8 fitted with a vent 9. After 2 minutes, the majority of [$^{18}$F]2-fluoroethylazide has distilled with acetonitrile as carrier.

The decay corrected radiochemical yield of [$^{18}$F]2-fluoroethylazide is 50%±7% (n=10) with a radiochemical purity of >99%. The corrected distillation efficiency of the apparatus is 71%±4% (n=10).

What is claimed is:

1. A method for purifying a radiolabelled compound which comprises (i) passing a crude reaction mixture comprising the desired radiolabelled compound and one or more contaminants in a solvent through a narrow bore vessel at elevated temperature such that the solvent and either the radiolabelled compound or one or more contaminants is vaporised forming a vaporised component, and (ii) collecting the resulting vaporised component by condensing into a collection vessel, wherein the internal diameter of the narrow bore vessel is in the range of about 1 micrometer to 1.5 mm and wherein the radiolabelled compound has a boiling point of 200° C. or more.

2. A method according to claim 1 wherein the narrow bore vessel is an HPLC loop with no solid support packing.

3. A method according to claim 1 wherein the internal diameter of the narrow bore vessel is in the range of about 40 to 200 μm.

4. A method according to claim 1 wherein the radiolabelled compound is a radiolabelled tracer is either a [$^{18}$F]-tracer wherein said [$^{18}$F]-tracer is -[$^{18}$F]-FDG, [$^{18}$F]-FLT, [$^{18}$F]-FET, [$^{18}$F]-FES, or [$^{18}$F]-FHBG, or a [$^{11}$C]-tracer wherein said [$^{11}$C]-tracer is [$^{11}$C]-PIB, [$^{11}$C]-CFT, [$^{11}$C]-Raclopride, or [$^{11}$C]-thymidine.

\* \* \* \* \*